(12) United States Patent
Kostrzewski (10) Patent No.: US 8,292,156 B2
(45) Date of Patent: *Oct. 23, 2012

(54) VARYING TISSUE COMPRESSION AIDED BY ELASTIC MEMBERS

(75) Inventor: Stanislaw Kostrzewski, Newtown, CT (US)

(73) Assignee: Tyco Healthcare Group LP, Mansfield, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/414,335

(22) Filed: Mar. 7, 2012

(65) Prior Publication Data

US 2012/0160895 A1    Jun. 28, 2012

Related U.S. Application Data

(63) Continuation of application No. 12/578,847, filed on Oct. 14, 2009, now Pat. No. 8,152,041.

(51) Int. Cl.
*A61B 17/068* (2006.01)
(52) U.S. Cl. ........................................ 227/176.1; 227/19
(58) Field of Classification Search ............ 227/19, 227/176.1, 175.1, 180.1, 178.1; 606/139, 606/219
See application file for complete search history.

(56) References Cited

U.S. PATENT DOCUMENTS

| | | | |
|---|---|---|---|
| 3,771,526 A | 11/1973 | Rudie | |
| 4,319,576 A | 3/1982 | Rothfuss | |
| 4,475,679 A | 10/1984 | Fleury, Jr. | |
| 4,605,001 A | 8/1986 | Rothfuss et al. | |
| 4,608,981 A | 9/1986 | Rothfuss et al. | |
| 4,610,383 A | 9/1986 | Rothfuss et al. | |
| 4,741,336 A | 5/1988 | Failla et al. | |
| 4,767,044 A | 8/1988 | Green | |
| 4,809,695 A | 3/1989 | Gwathmey et al. | |
| 4,848,637 A | 7/1989 | Pruitt | |
| 4,930,503 A | 6/1990 | Pruitt | |
| 4,941,623 A | 7/1990 | Pruitt | |
| 4,978,049 A | 12/1990 | Green | |
| 5,027,834 A | 7/1991 | Pruitt | |
| 5,108,422 A | 4/1992 | Green et al. | |
| 5,180,092 A | 1/1993 | Crainich | |
| 5,201,746 A | 4/1993 | Shichman | |
| 5,219,353 A | 6/1993 | Garvey, III et al. | |
| 5,240,163 A | 8/1993 | Stein et al. | |

(Continued)

FOREIGN PATENT DOCUMENTS

EP    0878169    11/1998

(Continued)

OTHER PUBLICATIONS

European Search Report for EP 10251797.6-2310 date of completion is Jan. 19, 2011 (3 pages).

(Continued)

*Primary Examiner* — Scott A. Smith (57) ABSTRACT

The present disclosure relates to surgical fastener applying apparatus, and the application of variable compression to tissue. More specifically, the presently disclosed surgical fastener applying apparatus including a first jaw having proximal and distal ends and including an anvil member, the anvil member extending along a longitudinal axis and including a tissue contacting surface and a second jaw having proximal and distal ends movably coupled to the first jaw, the second jaw including a cartridge member and a channel. The surgical fastener applying apparatus further includes a pair of elastic members positioned between the cartridge member and the channel of the second jaw, the pair of elastic members configured and dimensioned to apply and maintain constant compressive forces to tissue regardless of tissue thickness.

11 Claims, 9 Drawing Sheets

U.S. PATENT DOCUMENTS

| | | | |
|---|---|---|---|
| 5,282,829 A | 2/1994 | Hermes | |
| 5,342,396 A | 8/1994 | Cook | |
| 5,350,400 A | 9/1994 | Esposito et al. | |
| 5,452,836 A | 9/1995 | Huitema et al. | |
| 5,452,837 A | 9/1995 | Williamson, IV et al. | |
| 5,484,095 A | 1/1996 | Green et al. | |
| 5,497,931 A | 3/1996 | Nakamura | |
| 5,501,693 A | 3/1996 | Gravener | |
| 5,509,920 A | 4/1996 | Phillips et al. | |
| 5,571,116 A | 11/1996 | Bolanos | |
| 5,571,285 A | 11/1996 | Chow et al. | |
| 5,634,926 A | 6/1997 | Jobe | |
| 5,667,526 A | 9/1997 | Levin | |
| 5,667,527 A | 9/1997 | Cook | |
| 5,676,674 A | 10/1997 | Bolanos et al. | |
| 5,697,542 A | 12/1997 | Knodel et al. | |
| 5,709,680 A | 1/1998 | Yates et al. | |
| 5,741,268 A | 4/1998 | Schutz | |
| 5,810,822 A | 9/1998 | Mortier | |
| 5,865,361 A | 2/1999 | Milliman et al. | |
| 5,871,135 A | 2/1999 | Williamson, IV et al. | |
| 5,915,616 A | 6/1999 | Viola et al. | |
| 5,964,394 A | 10/1999 | Robertson | |
| 6,010,054 A | 1/2000 | Johnson et al. | |
| 6,083,242 A | 7/2000 | Cook | |
| 6,202,914 B1 | 3/2001 | Geiste et al. | |
| 6,325,810 B1 | 12/2001 | Hamilton et al. | |
| 6,348,054 B1 | 2/2002 | Allen | |
| 6,786,382 B1 | 9/2004 | Hoffman | |
| 6,905,057 B2 | 6/2005 | Swayze et al. | |
| 6,959,852 B2 | 11/2005 | Shelton, IV et al. | |
| 6,964,363 B2 | 11/2005 | Wales et al. | |
| 6,978,921 B2 | 12/2005 | Shelton, IV et al. | |
| 6,978,922 B2 | 12/2005 | Bilotti et al. | |
| 6,988,649 B2 | 1/2006 | Shelton, IV et al. | |
| 7,000,818 B2 | 2/2006 | Shelton, IV et al. | |
| 7,000,819 B2 | 2/2006 | Swayze et al. | |
| 7,044,352 B2 | 5/2006 | Shelton, IV et al. | |
| 7,055,731 B2 | 6/2006 | Shelton, IV et al. | |
| 7,059,508 B2 | 6/2006 | Shelton, IV et al. | |
| 7,070,083 B2 | 7/2006 | Jankowski | |
| 7,401,721 B2 | 7/2008 | Holsten et al. | |
| 7,455,676 B2 | 11/2008 | Holsten et al. | |
| 7,481,348 B2 | 1/2009 | Marczyk | |
| 7,815,091 B2 | 10/2010 | Marczyk | |
| 2004/0004105 A1 | 1/2004 | Jankowski | |
| 2004/0073222 A1 | 4/2004 | Koseki | |
| 2004/0232195 A1 | 11/2004 | Shelton et al. | |
| 2004/0232199 A1 | 11/2004 | Shelton et al. | |
| 2004/0247415 A1 | 12/2004 | Mangone, Jr. | |
| 2005/0006430 A1 | 1/2005 | Wales | |
| 2005/0006431 A1 | 1/2005 | Shelton et al. | |
| 2005/0006434 A1 | 1/2005 | Wales et al. | |
| 2005/0023324 A1 | 2/2005 | Doll et al. | |
| 2005/0023325 A1 | 2/2005 | Gresham et al. | |
| 2005/0070925 A1 | 3/2005 | Shelton, IV et al. | |
| 2005/0070958 A1 | 3/2005 | Swayze et al. | |
| 2005/0173490 A1 | 8/2005 | Shelton, IV | |
| 2005/0178813 A1 | 8/2005 | Swayze et al. | |
| 2005/0187576 A1 | 8/2005 | Whitman et al. | |
| 2005/0263562 A1 | 12/2005 | Shelton, IV et al. | |
| 2005/0267530 A1 | 12/2005 | Cummins | |
| 2006/0000868 A1 | 1/2006 | Shelton, IV et al. | |
| 2006/0015144 A1 | 1/2006 | Burbank et al. | |
| 2006/0022014 A1 | 2/2006 | Shelton, IV et al. | |
| 2006/0022015 A1 | 2/2006 | Shelton, IV et al. | |
| 2006/0025809 A1 | 2/2006 | Shelton, IV | |
| 2006/0025810 A1 | 2/2006 | Shelton, IV | |
| 2006/0025811 A1 | 2/2006 | Shelton, IV | |
| 2006/0025812 A1 | 2/2006 | Shelton, IV | |
| 2006/0025813 A1 | 2/2006 | Shelton, IV et al. | |
| 2006/0025816 A1 | 2/2006 | Shelton, IV | |
| 2006/0025817 A1 | 2/2006 | Ortiz et al. | |
| 2006/0039779 A1 | 2/2006 | Ring | |
| 2006/0049230 A1 | 3/2006 | Shelton, IV et al. | |
| 2006/0097026 A1 | 5/2006 | Shelton, IV | |
| 2006/0124688 A1 | 6/2006 | Racenet et al. | |
| 2006/0226196 A1 | 10/2006 | Huell et al. | |
| 2007/0010838 A1 | 1/2007 | Shelton, IV et al. | |
| 2007/0131732 A1 | 6/2007 | Holsten et al. | |
| 2007/0262116 A1 | 11/2007 | Hueil et al. | |
| 2008/0041918 A1 | 2/2008 | Holsten et al. | |
| 2008/0078804 A1 | 4/2008 | Shelton et al. | |

FOREIGN PATENT DOCUMENTS

| | | |
|---|---|---|
| EP | 0640315 | 12/1998 |
| EP | 1090592 | 4/2001 |
| EP | 1316290 | 6/2003 |
| EP | 1479346 | 11/2004 |
| EP | 1754445 A2 | 2/2007 |
| EP | 1785098 A2 | 5/2007 |
| FR | 2838952 | 10/2003 |
| SU | 405234 | 9/1975 |
| SU | 1333319 | 8/1987 |
| SU | 1442191 | 12/1988 |
| SU | 1459659 | 2/1989 |
| WO | WO 86/02254 A1 | 4/1986 |
| WO | WO 90/05489 | 5/1990 |
| WO | WO 97/34533 | 9/1997 |
| WO | WO 03/094743 | 11/2003 |
| WO | WO 03/094747 | 11/2003 |
| WO | WO 2008/039250 A1 | 4/2008 |

OTHER PUBLICATIONS

International Search Report from EP Application No. 07 25 4366 dated Nov. 11, 2010.

International Search Report from EP Application No. 09 25 1067 mailed Mar. 17, 2011.

European Search Report for EP 06016963.8-2318 date of completion is Mar. 9, 2007.

VARYING TISSUE COMPRESSION AIDED BY ELASTIC MEMBERS

CROSS-REFERENCE TO RELATED APPLICATIONS

This application is a continuation of U.S. application Ser. No. 12/578,847 filed Oct. 14, 2009, now U.S. Pat. No. 8,152,041 and the disclosures of each of the above-identified applications are hereby incorporated by reference in their entirety.

BACKGROUND

1. Technical Field

The present disclosure relates to a surgical fastener applying apparatus. More particularly, the present disclosure relates to a tool assembly for use with a surgical fastener applying apparatus, and methods of using the same, to apply a plurality of surgical fasteners to tissue with varying compressive forces. The present disclosure also relates to elastic members to apply and maintain constant compressive forces to tissue regardless of tissue thickness.

2. Background of the Related Art

There are several known types of surgical stapling instruments specifically adapted for use in various procedures such as end-to-end anastomosis, gastrointestinal anastomosis, endoscopic gastrointestinal anastomosis, and transverse anastomosis. Examples of stapling instruments for these various procedures can be found in U.S. Pat. Nos. 5,915,616; 6,202,914; 5,865,361; and 5,964,394.

Each surgical stapling instrument includes an anvil which is approximated relative to a staple cartridge. The staple cartridge typically has one or more laterally spaced rows of staples which, depending on the particular stapling instrument, may be arranged in a linear or non-linear configuration. The anvil includes staple forming depressions which are aligned with and/or in registration with the staple slots of the staples in the cartridge. In use, each of the surgical stapling instruments involves the gripping of tissue to be fastened, the ejecting of individual staples, the forcing of staples through the gripped tissue and the closing and/or forming of the staples against the staple forming depressions of the anvil.

A common issue in transecting tissue and/or in anastomosis procedures, employing any one of the surgical stapling instruments disclosed above, is the balance between anastomotic strength and the degree of hemostasis achievable. It is known to include different size staples in a surgical stapling apparatus having a constant gap (i.e., a uniform distance) between an anvil and a staple cartridge.

SUMMARY

The present disclosure relates to surgical fastener applying apparatus including a first jaw having proximal and distal ends and including an anvil member, the anvil member extending along a longitudinal axis and including a tissue contacting surface and a second jaw having proximal and distal ends movably coupled to the first jaw, the second jaw including a cartridge member and a channel. The surgical fastener applying apparatus further includes a pair of elastic members positioned between the cartridge member and the channel of the second jaw, the pair of elastic members configured and dimensioned to apply and maintain constant compressive forces to tissue regardless of tissue thickness.

The elastic members can be configured and dimensioned such that longitudinal relative movement between the cartridge member and the channel is fully restricted. The elastic members may be configured and dimensioned such that transversal movement between the cartridge member and the channel is permitted. The transversal movement may be determined by a size of the cartridge member and the channel.

In certain embodiments, when the first jaw and the second jaw are in an opened position, the pair of elastic members maintain the cartridge member separate from the channel defined by the second jaw. When the first jaw and the second jaw are in a closed position, the pair of elastic members are compressed to create a tissue gap proportional to a generated clamping force. In certain embodiments, a staple formation resulting from the closed position is independent of tissue formation and depends on the channel defined by the second jaw, one or more pushers, and a knife's I-beam configuration. The surgical fastener applying apparatus can further include a plurality of surgical fasteners positioned within the cartridge member, each surgical fastener having a substantially equivalent height.

The pair of elastic members can be formed of a substantially resilient material to support layers of tissue positioned between the first and second jaws. The pair of elastic members may be fixedly secured to the cartridge member. In certain embodiments, the pair of elastic members are releasably secured to the cartridge member.

The pair of elastic members may be disposed parallel to each other and extend a portion of a length of the cartridge member and the channel. The pair of elastic members can be positioned on an outer edge of the cartridge member and the channel.

These and other features of the surgical access apparatus and elastic members disclosed herein will become more readily apparent to those skilled in the art through reference to the detailed description of various embodiments of the present disclosure that follows.

BRIEF DESCRIPTION OF THE DRAWINGS

Various embodiments of the present disclosure are described herein below with references to the drawings, wherein.

DETAILED DESCRIPTION OF THE EMBODIMENTS

Various embodiments of the presently disclosed surgical fastener applying apparatus, and methods of using the same, will now be described in detail with reference to the drawings wherein like references numerals identify similar or identical elements. In the drawings, and in the description which follows, the term "proximal" will refer to the end the surgical fastener applying apparatus, or component thereof, that is closer to the operator during use, while the term "distal" will refer to the end that is further from the operator, as is traditional and conventional in the art. In addition, the term "surgical fastener" should be understood to include any substantially rigid structure formed of a biocompatible material that is suitable for the intended purpose of joining tissue together, including but not being limited to surgical staples, clips, and the like.

Figure 1:
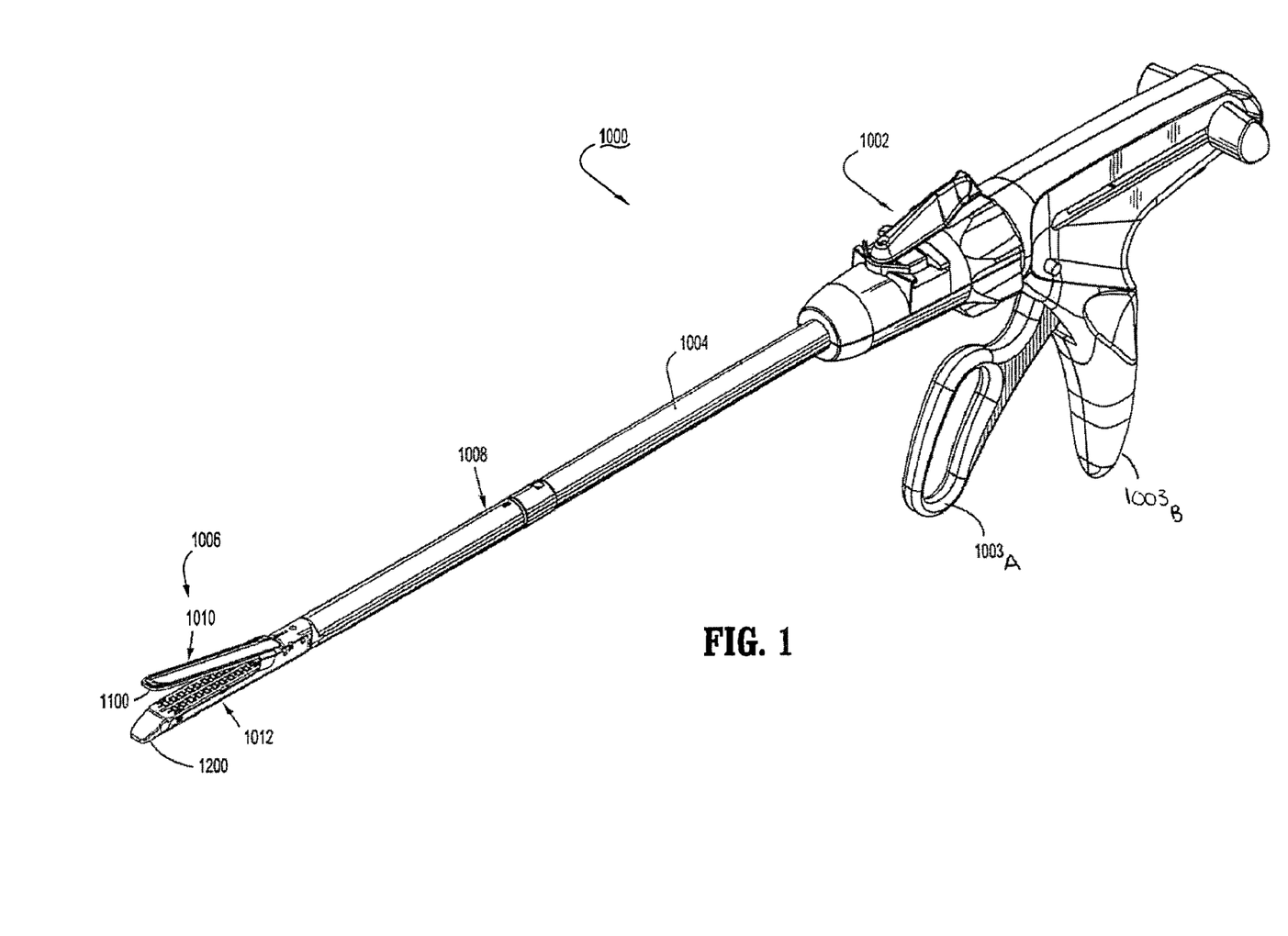
FIG. 1 is a top, perspective view of a surgical fastener applying apparatus having a tool assembly at a distal end thereof for applying a plurality of surgical fasteners to tissue, according to one embodiment of the present disclosure.

FIG. 1 illustrates a surgical fastener applying apparatus 1000, of either the re-usable or disposable variety, including a handle assembly 1002 with a movable handle $1003_A$ and a stationary handle $1003_B$, an elongated shaft 1004 extending distally from the handle assembly 1002, and a tool assembly 1006 that is coupled to a distal end 1008 of the elongated shaft 1004.

In various embodiments, it is envisioned that the handle assembly 1002 may include motor-driven, hydraulic, ratcheting, or other such mechanisms. In general, the tool assembly 1006 is adapted to clamp, fasten together, and sever adjacent tissue segments along a cut-line. During use, the surgical fastener applying apparatus 1000 is approximated and fired similarly to, and in accordance with other known surgical fastener applying apparatus. A discussion of the approximation and firing of surgical fastener applying apparatus 1000, including the components and interaction of the handle assembly 1002 and included drive assembly, is provided below.

Referring now to FIGS. 1-6, the tool assembly 1006 includes a first jaw 1010 that is pivotally coupled to a second jaw 1012 to facilitate approximation thereof The first jaw 1010 of the tool assembly 1006 includes an anvil 1100, and the second jaw 1012 includes a surgical fastener cartridge 1200 that is loaded with a plurality of surgical fasteners 100.

Pivoting the movable handle $1003_A$ towards the stationary handle $1003_B$ approximates the first jaw 1010 towards the second jaw 1012 (see FIG. 1). After the jaws 1010, 1012 are in close operative alignment, continued pivoting of the movable handle $1003_A$ ejects the plurality of surgical fasteners 100 from the surgical fastener cartridge 1200 such that the plurality of surgical fasteners 100 are driven into the anvil 1100, thus being formed into completed surgical fasteners, as described in further detail below. The cartridge 1200 in certain embodiments is removable and replaceable with another loaded cartridge. In other embodiments, the tool assembly 1006 comprises or forms a part of a removable and replaceable loading unit for the surgical fastener applying apparatus 1000. Further details regarding ejection of the surgical fasteners 100 is provided below with reference to FIG. 2.

Figure 2:
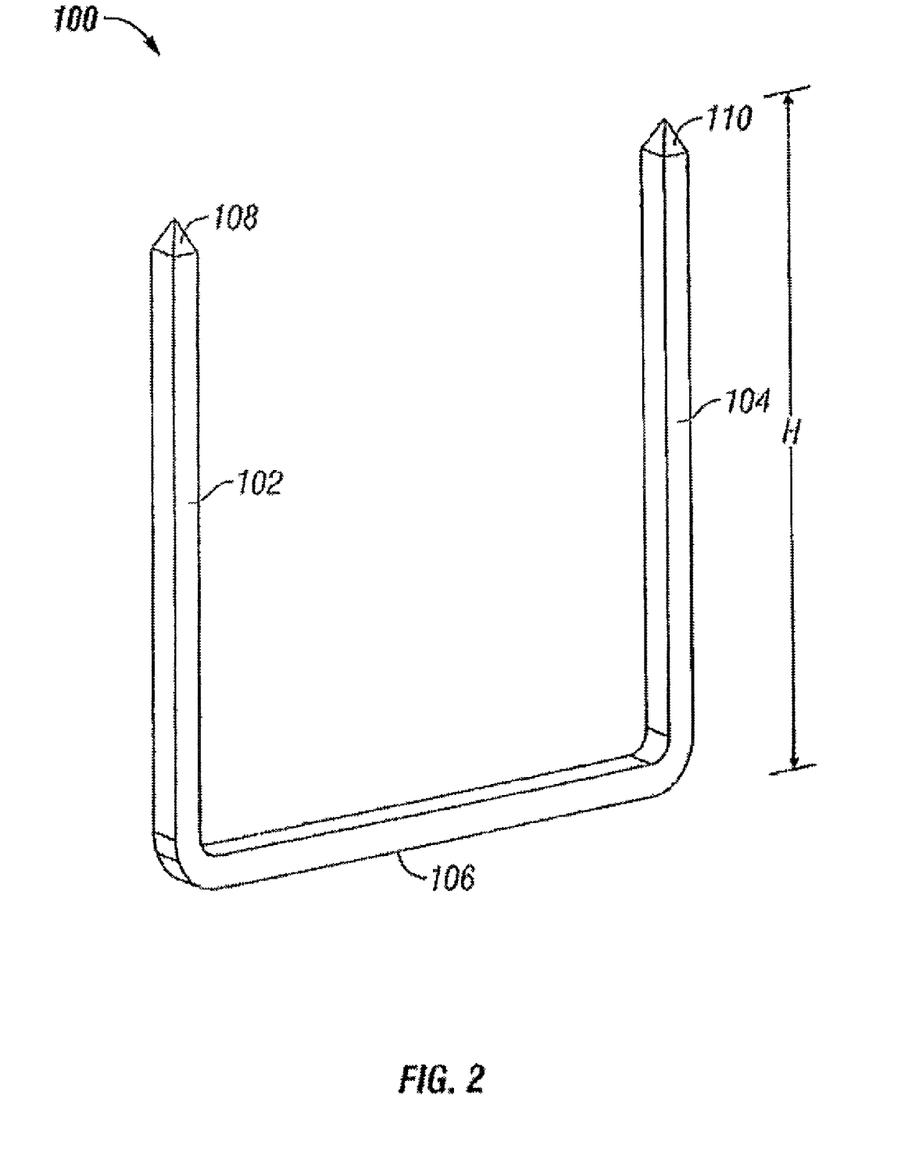
FIG. 2 is a side, perspective view of a surgical fastener, according to the present disclosure.

Each surgical fastener 100 includes two legs 102, 104 that are connected by a backspan 106 extending therebetween (see FIG. 2). The legs 102, 104 extend from the backspan 106 to respective penetrating ends 108, 110 such that each surgical fastener 100 defines a substantially equivalent height "H" prior to formation. The dimensions of the backspan 106 and the legs 102, 104 can be varied such that the surgical fastener 100 may be used to fasten tissue having varying attributes, such as the thickness thereof or the presence of scar tissue.

The legs 102, 104 and the backspan 106 may define a cross-section having any suitable geometric configuration including, but not limited to, rectangular, oval, square, triangular, trapezoidal, etc. The legs 102, 104 and the backspan 106 may exhibit the same geometrical configuration, as shown in FIG. 2, or alternatively, the legs 102, 104 and the backspan 106 may exhibit different geometrical configurations. For example, the legs 102, 104 may exhibit a rectangular cross-section, whereas the backspan 106 may exhibit an oval cross-section.

The respective penetrating ends 108, 110 of the legs 102, 104 may be tapered to facilitate the penetration of tissue, or alternatively, the penetrating ends 108, 110 may not include a taper. In various embodiments, it is also envisioned that the penetrating ends 108, 110 may define either a conical surface, or flat surface.

Prior to formation, the legs 102, 104 of each surgical fastener 100 may extend from the backspan 106 such that they are substantially parallel. In the alternative, the legs 102, 104 may converge or diverge from the backspan 106.

Figure 3:
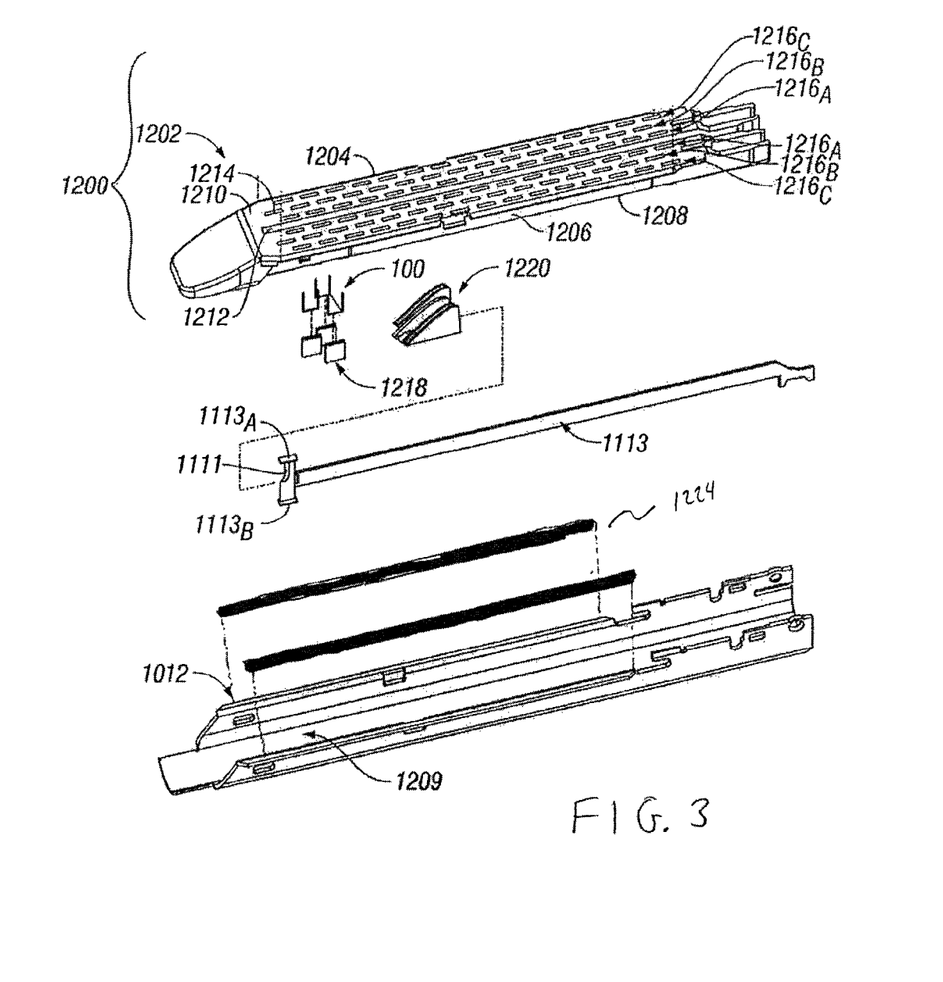
FIG. 3 is a partial perspective view of the tool assembly seen in FIG. 1 with parts separated illustrating an anvil and a surgical fastener cartridge including a pair of elastic members, according to the present disclosure.
Figure 3A:
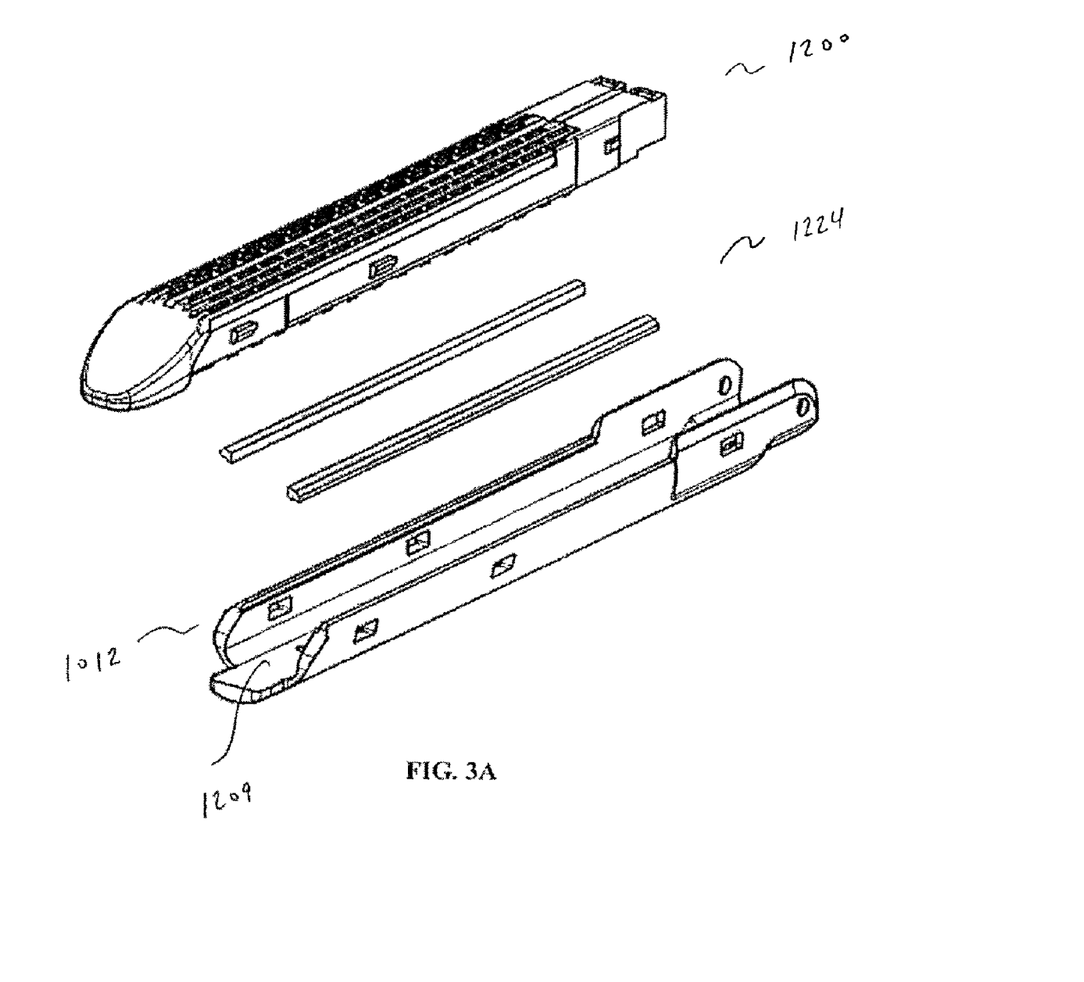
FIG. 3A is a partial exploded view of the tool assembly of FIG. 1 with parts separated illustrating the cartridge, the elastic members, and the second jaw defining a channel, according to the present disclosure.
Figure 4:
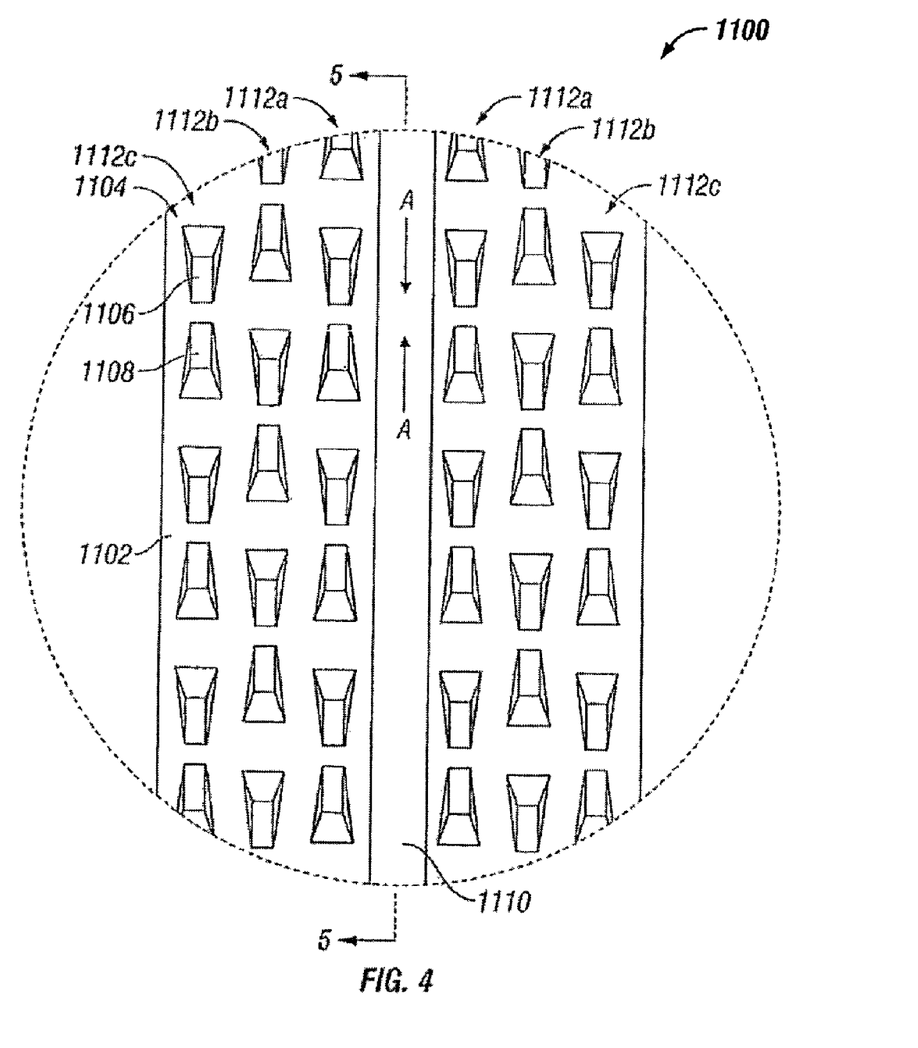
FIG. 4 is a schematic, enlarged view of the area of detail indicated in FIG. 3 illustrating a tissue contacting surface of the anvil and a plurality of pockets formed therein.
Figure 5:
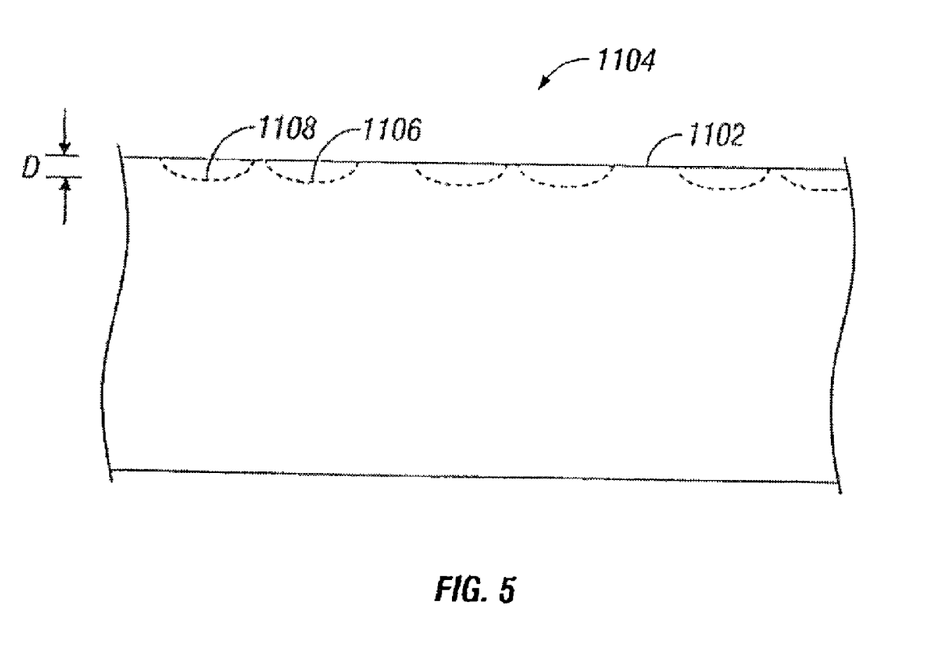
FIG. 5 is a longitudinal, cross-sectional view taken along line 5-5 in FIG. 4 illustrating the pockets formed in the tissue contacting surface of the anvil.
Figure 7:
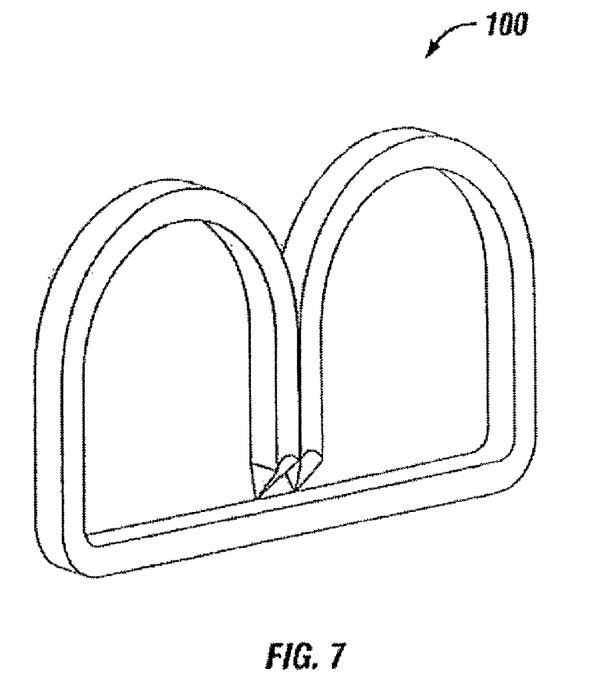
FIG. 7 is a side, perspective view of the surgical fastener shown in FIG. 2 exhibiting a standard "B" shaped configuration subsequent to formation through engagement with the pockets formed in the anvil seen in FIG. 3.
Figure 8:
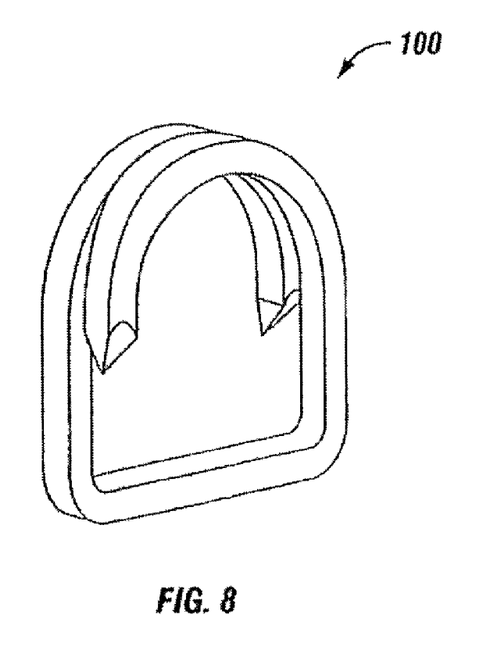
FIG. 8 is side, perspective view of a surgical fastener having a single-loop configuration subsequent to formation through contact with the pockets formed in the tissue contacting surface of an alternative embodiment of the anvil seen in FIG. 3.

With reference now to FIGS. 3-5 in particular, the anvil 1100 will be discussed. The anvil 1100 is an elongated member having a tissue contacting surface 1102 with a plurality of pockets 1104 formed therein. Each of the pockets 1104 is positioned to receive and deform the legs 102, 104 of a surgical fastener 100 (see FIG. 2) to achieve a formed configuration. More particularly, each pocket 1104 formed in the anvil 1100 includes two forming surfaces 1106, 1108 that extend into the anvil 1100, i.e., away from the tissue contacting surface 1102, to define a depth "D", as best seen in FIG. 5. Upon engagement of the legs 102, 104 with the forming surfaces 1106, 1108, the forming surfaces 1106, 1108 guide the legs 102, 104 inwardly in the direction of arrows "A" (see FIG. 4) to facilitate deformation of the surgical fastener 100 into a standard "B" shaped configuration (see FIG. 7). In an alternative embodiment, the anvil 1100 may include pockets 1104 that are configured and dimensioned to deform the surgical fastener 100 such that the fastener 100 defines a single-loop configuration (see FIG. 8) upon formation. It is also envisioned that the surgical fasteners 100 may exhibit other configurations upon formation.

The pockets 1104 are arranged into rows disposed on opposite sides of a slot 1110 extending through the anvil 1100 (see FIGS. 3, 4). The slot 1110 is configured to accommodate movement of a knife 1111, or other such cutting element, such that tissue may be severed along a cut-line. Although the slot 1110 is depicted as extending longitudinally through the anvil 1100, in alternative embodiments, the slot 1110 may define a configuration that is angled, arcuate, or shaped otherwise. The slot 1110 may extend along a centerline of the anvil 1100, as shown in the embodiment illustrated in FIGS. 3 and 4, or alternatively, the slot 1110 may be offset from the centerline of the anvil 1100.

The anvil 1100 includes a pair of inner rows $1112_A$, a pair of intermediate rows $1112_B$, and a pair of outer rows $1112_C$ (see FIG. 4). The inner pair of rows $1112_A$ are spaced laterally outward of the slot 1110 and are closest thereto, the pair of intermediate rows $1112_B$ are spaced laterally outward from the pair of inner rows $1112_A$, and the pair of outer rows $1112_C$ are spaced laterally outward from the pair of intermediate rows $1112_B$ and are furthest from the slot 1110. While the anvil 1100 is depicted as including three pairs of rows, i.e., the respective pairs of inner, intermediate, and outer rows $1112_A$, $1112_B$, $1112_C$, fewer and greater numbers of rows of pockets 1104 may be included in alternative embodiments of the anvil 1100.

With continued reference to FIGS. 3-5, the surgical fastener cartridge 1200 will be described. The surgical fastener cartridge 1200 includes a cartridge body 1202 with a pair of side walls 1204, 1206, a bottom wall 1208, and a top wall 1210 (see FIG. 3), and resides in a channel 1209 defined by the second jaw 1012. The cartridge body 1202 includes a slot 1212 extending therethrough that is configured to accommodate longitudinal movement of the knife 1111 (see FIG. 3). As discussed above with respect to the anvil 1100, while the slot 1212 is depicted as extending longitudinally through the surgical fastener cartridge 1200, in alternative embodiments, the slot 1212 may define a configuration that is angled, arcuate, or shaped otherwise. The slot 1212 is arranged to correspond with the slot in the anvil 1100. The slot 1212 may extend along a centerline of the surgical fastener cartridge 1200, as shown in the embodiment illustrated in FIG. 3, or alternatively, the slot 1212 may be spaced therefrom.

The top wall 1210 of the cartridge body 1202 includes a plurality of retention slots 1214 (see FIG. 3) formed therein that are arranged into rows corresponding in position to the rows of pockets 1104 (see FIG. 4) formed in the tissue contacting surface 1102 of the anvil 1100. Accordingly, in the particular embodiment of the surgical fastener cartridge 1200 seen in FIG. 3, the top wall 1210 is substantially planar and parallel to the tissue contacting surface 1102 of the anvil. Also in FIG. 3, the retention slots 1214 are arranged into a pair of inner rows $1216_A$, a pair of intermediate rows $1216_B$, and a pair of outer rows 1216, each of which is disposed on opposite sides of the slot 1212. The pair of inner rows $1216_A$ are spaced laterally outward of the slot 1212 and are closest thereto, the pair of intermediate rows $1216_B$ are spaced laterally outward from the pair of inner rows $1216_A$, and the pair of outer rows $1216_C$ are spaced laterally outward from the pair of intermediate rows $1216_B$ and are furthest from the slot 1212. While the surgical fastener cartridge 1200 is depicted as including three pairs of rows, i.e., the respective inner, intermediate, and outer rows $1216_A$, $1216_B$, $1216_C$, fewer and greater numbers of rows of fastener retention slots 1214 may be included in alternative embodiments of the surgical fastener cartridge 1200. In certain embodiments, the surgical fastener cartridge 1200 does not include a slot for accommodating a knife.

Figure 9:
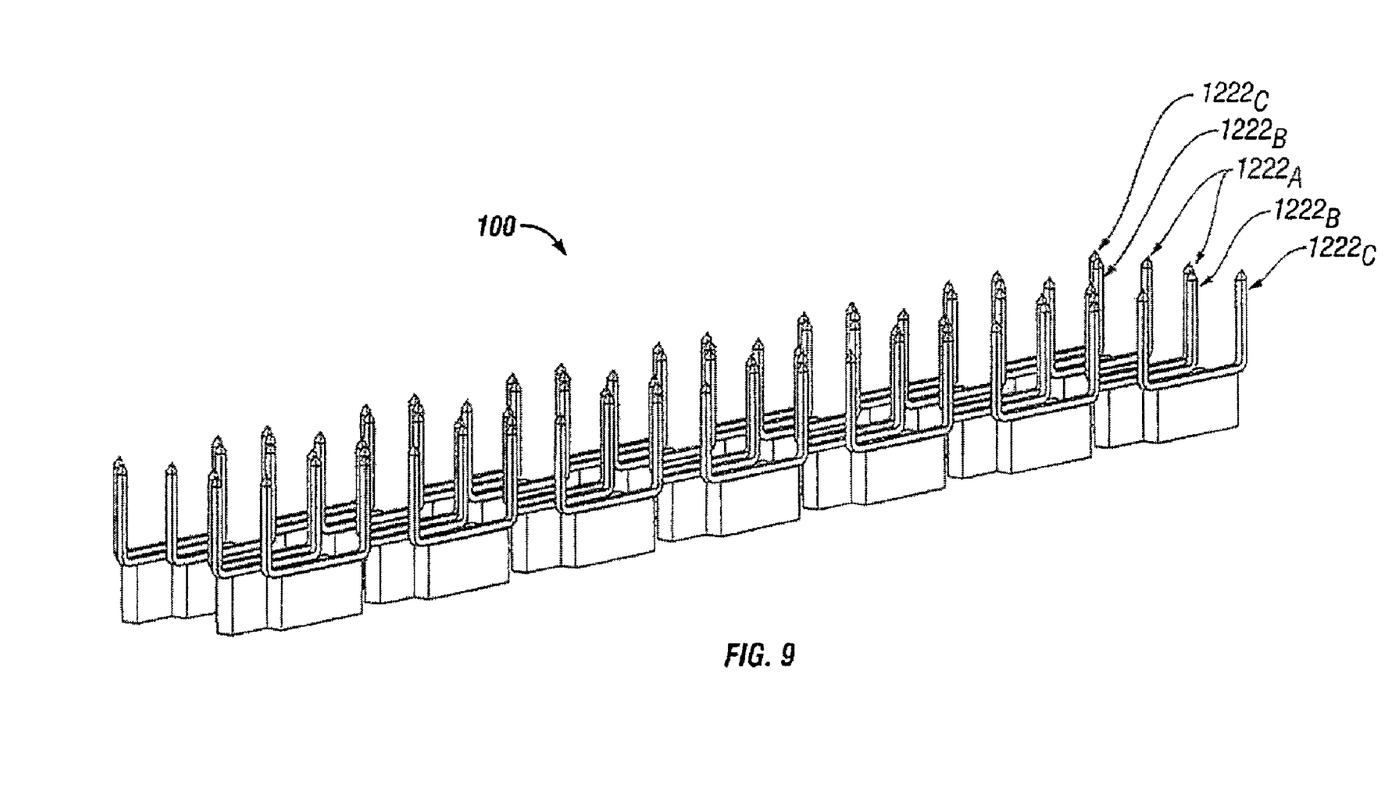
FIG. 9 is a partial longitudinal, perspective view, with parts removed, of the surgical fastener cartridge seen in FIG. 3 illustrating the plurality of surgical fasteners arranged into inner, intermediate, and outer rows.

Each fastener retention slot 1214 is configured and dimensioned to receive a surgical fastener 100 (see FIG. 3), as well as a correspondingly dimensioned pusher 1218 positioned therein. The pusher 1218 and the surgical fastener 100 are driven upwardly, i.e. towards the top wall 1210, by a sled 1220 (see FIG. 3), as discussed in further detail below. As the surgical fasteners 100 exit the fastener retention slots 1214, they are necessarily deployed in rows, i.e., respective inner, intermediate, and outer rows $1222_A$, $1222_B$, $1222_C$ (see FIG. 9), on opposite sides of the cut-line created in the tissue.

Figure 6:
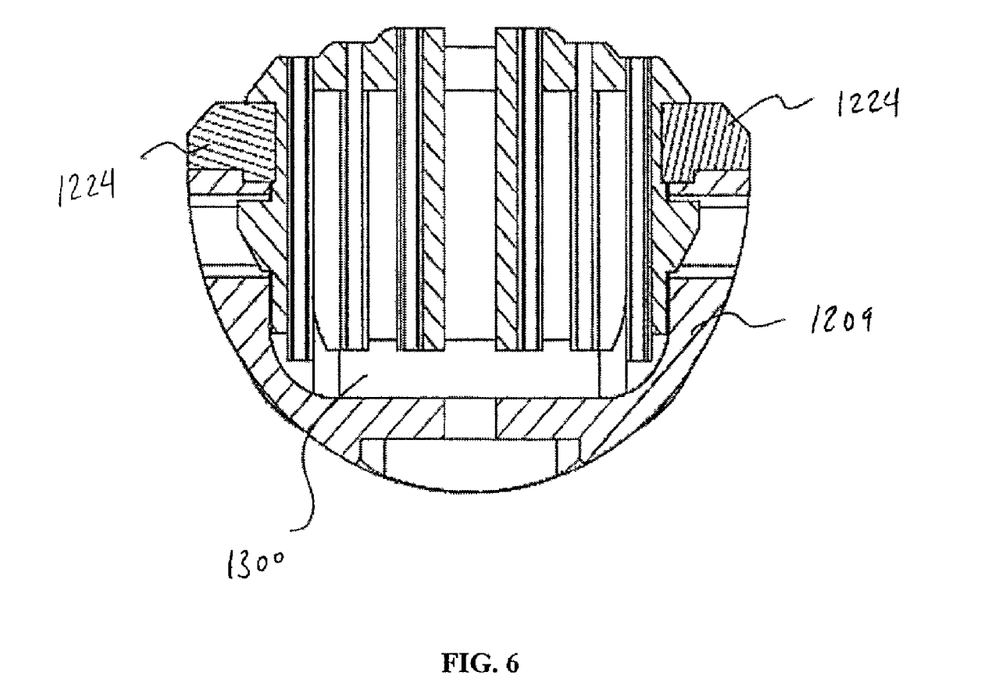
FIG. 6 is a lateral, cross-sectional view of the tool assembly seen in FIG. 1 taken through the pockets formed in the anvil and retention slots formed in the surgical fastener cartridge.

Referring now to FIGS. 3-6, the second jaw 1012 further includes a pair of elastic members 1224 that are configured and dimensioned to apply and maintain a constant compressive force to tissue positioned between the jaws 1010, 1012 (see FIG. 1) of the tool assembly 1006. In this embodiment, the pair of elastic members 1224 seen in FIGS. 3 and 6, are configured as two substantially parallel, elongate members that are positioned between the cartridge body 1202 and the edge of the channel 1209 defined by the second jaw 1012. The pair of elastic members 1224 are attached to, or otherwise disposed on, the edges of the channel 1209, and may be fixedly or releasably attached thereto in alternative embodiments.

The pair of elastic members 1224 may be formed from any suitable biocompatible material that is sufficiently resilient to support layers of tissue. The pair of elastic members 1224 may be formed of organic or synthetic material. The pair of elastic members 1224 may be configured as a buttress, fastener line reinforcement material, pledget, or other such materials. The pair of elastic members 1224 may be a bioabsorbable or non-absorbable material, pad of material, composite materials, materials including fibers, collagen or other materials derived from natural tissue. The pair of elastic members 1224 may include a plurality of elastic members of any shape or size or length or width or pattern depending on the desired application. Additionally, a plurality of elastic members may be positioned in any location with regards to the channel 1209 and the cartridge 1200.

The configuration of the pair of elastic members 1224 applies different pressure to tissue, depending upon the location of the tissue with respect to the pair of elastic members 1224. The configuration and dimensions of the pair of elastic members 1224 in FIGS. 3 and 6 are intended to maintain constant tissue clamping forces regardless of the tissue thickness. The pair of elastic members 1224, seen in FIGS. 3 and 6, facilitate the application of a compressive force to the tissue and can be configured, in certain embodiments, to maintain a constant force on the tissue to expend the range of Single Use Loading Unit (SULU) application. Accordingly, the pair of elastic members 1224 are placed between the outer lip of the surgical fastener cartridge 1200 and the edges of the channel 1209 defined by the second jaw 1012, thus creating a spring loaded cartridge. The pair of elastic members 1224 are fully trapped or embedded between the surgical fastener cartridge 1200 and the edges of the channel 1209 as a result of their cross-sectional shape.

The positioning of the pair of elastic members 1224 allows certain types of movement with regards to the surgical fastener cartridge 1200 and the edges of the channel 1209 defined by the second jaw 1012. Adding elastic members 1224 does not affect longitudinal alignment or movement relative to the cartridge 1200 and the channel 1209. However, transversal movement between the surgical fastener cartridge 1200 and the edges of the channel 1209 defined by the second jaw 1012 is permitted. The transversal movement is determined by the size of the surgical fastener cartridge 1200 and the channel 1209 interfacing features. The transversal movement is vertical movement, and not lateral movement.

Additionally, in the unclamped or open position, the pair of elastic members 1224 keep the surgical fastener cartridge 1200 away from the channel 1209 defined by the second jaw 1012. When in the clamped or closed position, the tissue is clamped between the first jaw 1010 and the second jaw 1012, such that the pair of elastic members 1224 are compressed, thus creating a tissue gap 1300 proportional to the generated clamping force. It is noted that staple formation remains unchanged regardless of the tissue thickness because it is not affected by the transversal movement of the surgical fastener cartridge 1200. In fact, the staple formation depends on one or more of the chain channel 1209, the sled 1220, the pusher 1218, the anvil 1100, and knife's 1111 I-beam configuration. As a result, the pair of elastic members 1224 (i) minimize clamping forces to prevent deformation of the SULU components in order to maintain a satisfactory tissue formation and (ii) widen the tissue thickness range.

Furthermore, the spacing inside the channel 1209 varies with compressive forces applied to the cartridge 1200. The bottom of the cartridges 1200 and the bottom portion of the channel 1209 define a gap 1300 that is proportional to the tissue thickness. As the tissue thickness increases between the first jaw 1010 and the second jaw 1012, the gap 1300 defined between the cartridge 1200 and the channel 1209 decreases, as stronger compressive forces are applied.

While the anvil 1100 (see FIGS. 1, 3), the surgical fastener cartridge 1200 (see FIGS. 1, 3), and the various embodiments thereof described herein above have been discussed in connection with a plurality of substantially uniform surgical fasteners 100 (see FIG. 2), in alternative embodiments of the present disclosure, the anvil 1100 and the surgical fastener cartridge 1200 may be adapted for use with a plurality of surgical fasteners having varying dimensions or configurations. For example, with reference to FIGS. 3 and 6, the pockets 1104 formed in the anvil 1100 and/or the retention slots 1214 formed in the surgical fastener cartridge 1200 may be configured and dimensioned to accommodate surgical fasteners having varying pre-formed heights "H" (see FIG. 2).

Additionally, although each embodiment of the anvil 1100 (see FIGS. 1, 3) and the surgical fastener cartridge 1200 (see FIGS. 1, 3) discussed herein above has been described as including corresponding slots 1110, 1212, respectively, that are configured and dimensioned to accommodate movement of the knife 1111 (see FIG. 3) subsequent to the fastening of tissue, the present disclosure also contemplates embodiments of the anvil 1100 and the surgical fastener cartridge 1200 that do not include such slots. In these embodiments, the tissue would be initially fastened and then severed subsequently thereafter, e.g., through the employ of a scalpel.

Referring now to FIGS. 1-6, a method of fastening tissue with the surgical fastener applying apparatus 1000 will be discussed. The surgical fastener applying apparatus 1000 is approximated and fired similarly to, and in accordance with other known surgical fastener applying apparatus, for example, the surgical fastener applying apparatus 1000 disclosed in commonly assigned U.S. Pat. No. 5,865,361, which is currently assigned to Tyco Healthcare Group LP, the disclosure of which is hereby incorporated by reference herein in its entirety.

As seen in FIG. 1, the handle assembly 1002 includes a movable handle member 1003$_A$. The movable handle 1003$_A$ is operatively connected to an actuation shaft, which receives the proximal end of a control rod such that linear advancement of the actuation shaft causes corresponding linear advancement of the control rod. An axial drive assembly is also provided that is engagable with the control rod. More specifically, the axial drive assembly includes an elongated drive beam 1113 with a distal end that supports the knife blade 1111 (see FIG. 3) that is configured and dimensioned for engagement with the control rod. As seen in FIG. 3, the knife 1111 is positioned to translate behind the sled 1220. The drive beam 1113 includes an upper flange 1113$_A$ that engages the slot 1110 formed in the anvil 1100, and a lower flange 1113$_B$ that engages the slot 1212 formed in the cartridge body 1202.

After the surgical fastener applying apparatus 1000 is manipulated such that the target tissue is disposed between the open jaws 1010, 1012 of the tool assembly 1006, the jaws 1010, 1012 are approximated using the handle assembly 1002 to clamp the target tissue therebetween and apply a compressive force thereto. Specifically, manipulation of the movable handle 1003$_A$ advances the actuation shaft to effectuate corresponding advancement of the control rod. In particular embodiments, the actuation shaft includes a toothed rack defined thereon, and the movable handle 1003$_A$ has a ratcheting pawl mounted thereto for incrementally engaging and advancing the actuation shaft. The pawl may be mounted on a pivot pin and a coiled torsion spring that biases the pawl into engagement with the toothed rack. The control rod is connected at its distal end to the drive assembly, which includes the aforementioned drive beam 1113, such that distal movement of control rod effects distal movement of the drive beam 1113, which in turn, forces the anvil 1100 towards the cartridge 1200. Specifically, the control rod advanced the drive beam 1113 distally such that the upper and lower flanges 1113$_A$, 1113$_B$ engage the slots 1110, 1212 of the anvil 1100 and the cartridge body 1202, respectively.

With the tissue securely clamped between the jaws 1010, 1012, the surgical fastener applying apparatus 1000 is then fired to eject the surgical fasteners by once again actuating the movable handle 1003$_A$. To fire the surgical fastener applying apparatus 1000, the movable handle 1003$_A$ is again manipulated to cause advancement of the drive assembly, which causes the sled 1220 (see FIG. 3) to traverse the cartridge body 1202 and engage the pushers 1218 (see FIG. 3) to thereby eject the plurality of surgical fasteners 100 from the surgical fastener cartridge 1200. Specifically, angled leading surfaces of the sled 1220 sequentially contact the pushers 1218 at cam surfaces included thereon as the sled translates. The interaction between the leading surfaces of the sled 1220 and the cam surfaces of the pushers 1218 urges the pushers 1218 towards the top wall 1210 of the cartridge body 1202. Sequential firing of the surgical fasteners 100 continues until the sled 1220 is advanced to the distal end of the cartridge 1200, at which time all of the surgical fasteners 100 housed the cartridge 1200 will have been ejected.

The plurality of surgical fasteners 100 pass through the retention slots 1214 (see FIGS. 3, 6) formed in the top wall 1210 of the surgical fastener cartridge 1200. After passing through the tissue, the plurality of surgical fasteners 100 are formed through engagement with the pockets 1104 (see FIGS. 3, 4, 6) defined in the tissue contacting surface 1102 of the anvil 1100 to achieve, for example, the standard "B" shaped configuration (see FIG. 7). Upon formation within the tissue, the plurality of surgical fasteners 100 act to maintain the compressive force applied thereto during clamping of the respective first and second jaws 1010, 1012 (see FIG. 1) of the tool assembly 1006.

Accordingly, the flow of blood through the tissue immediately adjacent and surrounding the cut-line will be less than the flow of blood through the tissue spaced laterally therefrom. More specifically, the tissue at the outer rows 1222C will be compressed less than the tissue at rows 1222B, and the tissue at rows 1222B will be compressed less than the tissue at rows 1222A (see FIG. 9). The flow of blood through the tissue surrounding the surgical fasteners 100 in rows 1222C will be less restricted when compared to the flow of blood through the tissue surrounding the surgical fasteners 100 in rows 1222B, and the flow of blood through the tissue surrounding the surgical fasteners 100 in rows 1222B will be less restricted when compared to the flow of blood through the tissue surrounding the surgical fasteners 100 in rows 1222A.

It is envisioned that the tool assembly 1006 may also be adapted for use with any of the other surgical fastener applying apparatus discussed in commonly owned U.S. Pat. Nos. 6,045,560; 5,964,394; 5,894,979; 5,878,937; 5,915,616; 5,836,503; 5,865,361; 5,862,972; 5,817,109; 5,797,538; and 5,782,396, the disclosures of which are hereby incorporated by reference herein in their entirety.

In certain embodiments of the present disclosure, it is envisioned that the disclosed surgical fastener applying apparatus may include a plurality of cam bars for interacting with the pushers to deploy the surgical fasteners. For example, the apparatus disclosed in commonly owned U.S. Pat. No. 5,318, 221, the disclosure of which is hereby incorporated by reference herein in its entirety, includes a cam bar adapter that holds a plurality of cam bars and a knife, as well as a channel that is advanced through operation of the handle of the apparatus, which drives the cam bars and knife forward. To clamp the anvil and the surgical fastener cartridge together, the apparatus further includes a clamp tube that is movable to surround the proximal end of the anvil.

As another example, the apparatus disclosed in U.S. Pat. No. 5,782,396, the disclosure of which is hereby incorporated by reference herein in its entirety, includes an actuation sled and an elongated drive beam that is advanced distally through operation of the handle of the apparatus, driving the actuation sled forward. In this apparatus, the distal end of the drive beam engages the anvil and the channel that supports the surgical fastener cartridge as the drive beam travels distally to deploy the staples and clamp the anvil and surgical fastener cartridge together.

The above description, disclosure, and figures should not be construed as limiting, but merely as exemplary of particular embodiments. It is to be understood, therefore, that the disclosure is not limited to the precise embodiments described, and that various other changes and modifications may be effected by one skilled in the art without departing from the scope or spirit of the disclosure. Additionally, those skilled in the art will appreciate that the elements and features illustrated or described in connection with one embodiment can be combined with those of another, and that such modifications and variations are also intended to be included within the scope of the present disclosure.

What is claimed is:

1. A surgical fastener applying apparatus, comprising:
a first jaw having proximal and distal ends and including an anvil member, the anvil member extending along a longitudinal axis;
a second jaw having a channel and a cartridge member disposed in the channel, the cartridge member having a plurality of surgical staples, the second jaw being movably coupled to the first jaw, the first jaw and the second jaw having an open position and a closed position; and
elastic material positioned between the cartridge member and the channel of the second jaw, the elastic material applying compressive forces to tissue clamped between the anvil member and the cartridge member when the first jaw and the second jaw are in the closed position, the elastic material being compressed when the first jaw and the second jaw are in the closed position to create a tissue gap according to a generated clamping force, the plurality of surgical staples being formed against the anvil member to a desired staple formation.

2. The surgical fastener applying apparatus of claim 1, wherein the elastic material comprises one or more elastic members.

3. The surgical fastener applying apparatus of claim 2, wherein the elastic material comprises a first elastic member disposed on a first lateral side of the channel and a second elastic member disposed on a second lateral side of the channel.

4. The surgical fastener applying apparatus of claim 2, wherein the staple formation is independent of tissue compression.

5. The surgical fastener applying apparatus of claim 1, wherein longitudinal relative movement between the cartridge member and the channel is fully restricted.

6. The surgical fastener applying apparatus of claim 1, wherein transversal movement between the cartridge member and the channel is permitted.

7. The surgical fastener applying apparatus of claim 6, wherein the transversal movement is determined by a size of the cartridge member and the channel.

8. The surgical fastener applying apparatus of claim 1, wherein when the first jaw and the second jaw are in the open position, the elastic material maintains the cartridge member separate from the channel.

9. The surgical fastener applying apparatus of claim 1, wherein the elastic material is formed of a substantially resilient material to support layers of tissue positioned between the first and second jaws.

10. The surgical fastener applying apparatus of claim 1, wherein the elastic material is fixedly secured to the cartridge member.

11. The surgical fastener applying apparatus of claim 1, wherein the elastic material is releasably secured to the cartridge member.

* * * * *